United States Patent [19]

Kramer et al.

[11] Patent Number: 5,451,210
[45] Date of Patent: Sep. 19, 1995

[54] SYSTEM AND METHOD FOR RAPID VASCULAR DRUG DELIVERY

[75] Inventors: George C. Kramer, Galveston; Herbert H. Spoon, San Antonio; Larry J. Miller, Spring Branch; David J. Collette; Rubén G. Zamorano, both of San Antonio; Joel P. Jenkinson, Galveston, all of Tex.

[73] Assignees: Lifequest Medical, Inc., San Antonio; Board of Regents, Univ. of TX System, Austin, both of Tex.

[21] Appl. No.: 168,823

[22] Filed: Dec. 17, 1993

Related U.S. Application Data

[60] Continuation-in-part of Ser. No. 958,279, Oct. 8, 1992, Pat. No. 5,271,744, which is a division of Ser. No. 692,674, Apr. 29, 1991, Pat. No. 5,176,643.

[51] Int. Cl.$^6$ .............................. A61M 5/20
[52] U.S. Cl. ............................. 604/137; 604/136
[58] Field of Search ........................ 604/136, 137

[56] References Cited

U.S. PATENT DOCUMENTS

| | | |
|---|---|---|
| 2,219,605 | 10/1940 | Turkel . |
| 2,634,726 | 4/1953 | Hanson . |
| 3,656,472 | 4/1972 | Movra ................ 604/136 |
| 3,797,489 | 3/1974 | Sarnoff . |
| 4,378,015 | 3/1983 | Wordman . |
| 4,445,510 | 6/1984 | Rigby . |
| 4,517,978 | 5/1985 | Levin et al. . |
| 4,530,695 | 7/1985 | Phillips et al. . |
| 4,578,064 | 3/1986 | Sarnoff et al. . |
| 4,675,004 | 7/1987 | Hadford . |
| 4,676,781 | 7/1987 | Phillips et al. . |
| 4,710,180 | 12/1987 | Johnson . |
| 4,787,891 | 11/1988 | Levin et al. ................ 604/136 |
| 4,790,830 | 12/1988 | Hamacher . |
| 4,838,877 | 6/1989 | Massau . |
| 4,850,967 | 7/1989 | Cosmai . |
| 4,894,055 | 1/1990 | Sudnak . |
| 4,900,311 | 2/1990 | Stern et al. . |
| 4,969,870 | 11/1990 | Kramer et al. . |
| 5,026,349 | 6/1991 | Schmitz et al. ............ 604/137 |
| 5,042,977 | 8/1991 | Bechtold et al. . |
| 5,085,641 | 2/1992 | Sarnoff et al. ............. 604/136 |
| 5,085,642 | 2/1992 | Sarnoff et al. ............. 604/136 |
| 5,092,843 | 3/1992 | Monroe et al. ............ 604/137 |
| 5,137,516 | 8/1992 | Rand et al. ................ 604/137 |
| 5,176,643 | 1/1993 | Kramer et al. . |
| 5,271,744 | 12/1993 | Kramer et al. . |

FOREIGN PATENT DOCUMENTS

WO88/08723 11/1988 Germany .

OTHER PUBLICATIONS

Halvorsen et al., "Evaluation of an Intraosseous Infusion Device for the Resuscitation of Huypovolemic Shock", *The Jr. of Trauma*, vol. 30, No. 6 (1990).

Primary Examiner—Paul J. Hirsch
Attorney, Agent, or Firm—Conley, Rose & Tayon

[57] ABSTRACT

A rapid vascular drug delivery device, system and method is provided having a releasibly extending and retracting needle necessary for injecting and withdrawing fluid into and from a physiological or non-physiological cavity. Accordingly, the needle can be releasibly extended with sufficient momentum at a point of impact to penetrate a hard substance such as bone. The needle is slideably placed within an aperture configured at the forward end of a main housing, wherein a trigger needle can be arranged proximate to the forward end in order to detect tissue thickness or bone depth necessary for ensuring accurate placement of the bone-piercing needle within the bone marrow. The needle can receive fluids interspersed by parallel-placed or series-placed fluid containers configured within the main housing. Thus, more than two dissimilar types of fluids or medicants can be pre-loaded into the device and delivered to the subject in order to enhance dissemination of, for example, a resuscitating drug deep within and throughout the bone marrow.

4 Claims, 12 Drawing Sheets

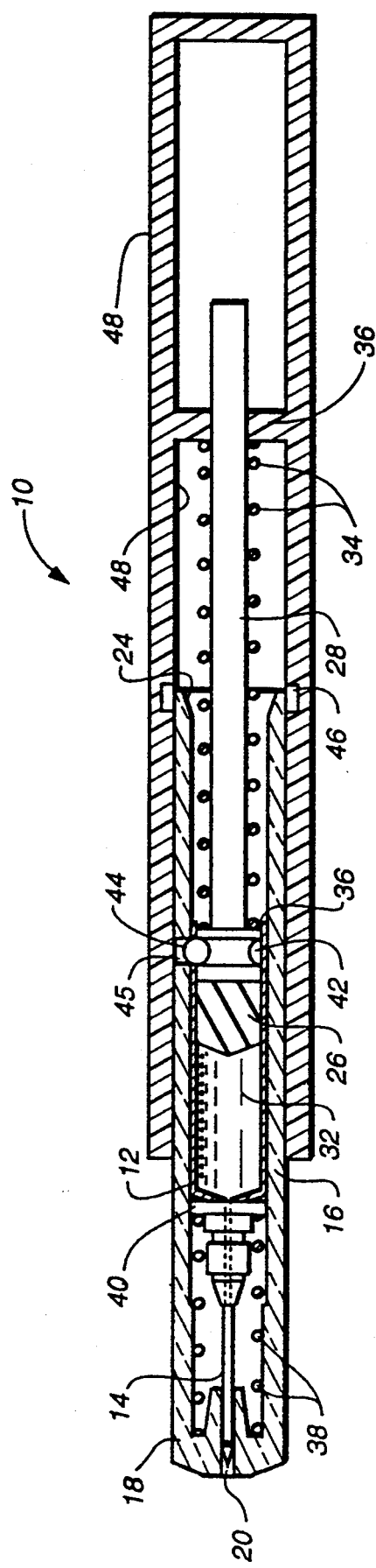
FIG._1
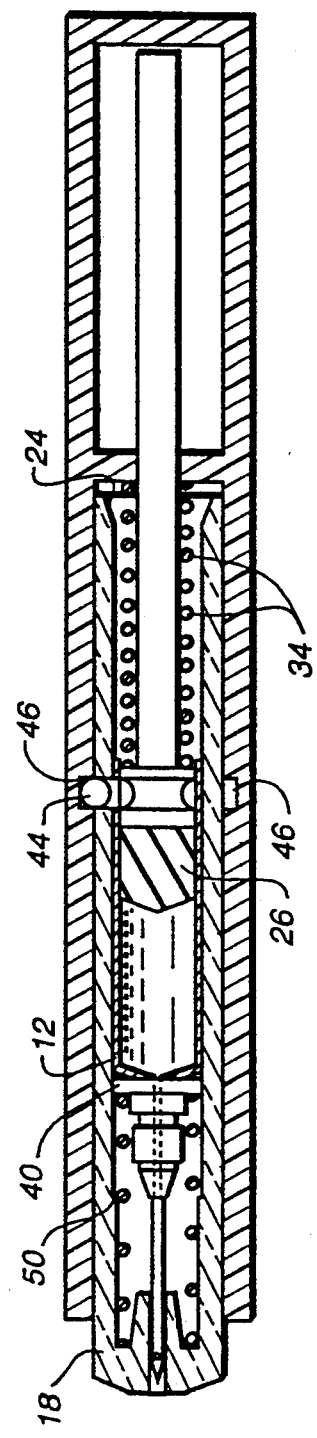
FIG._2

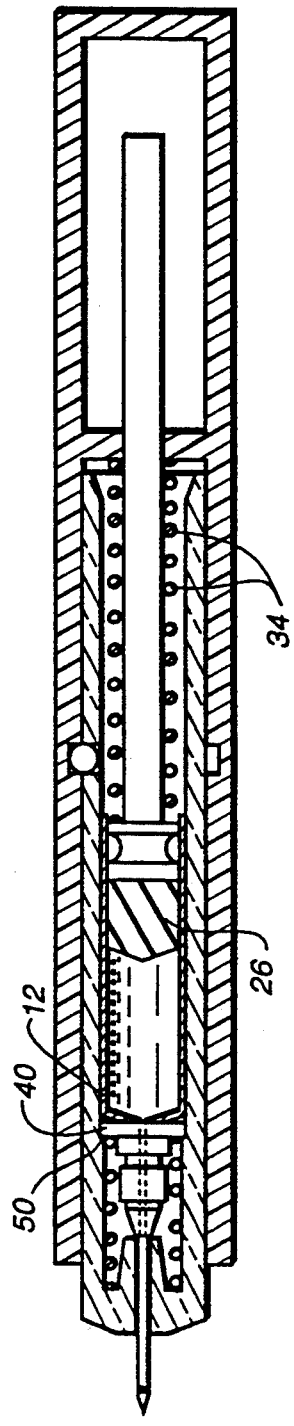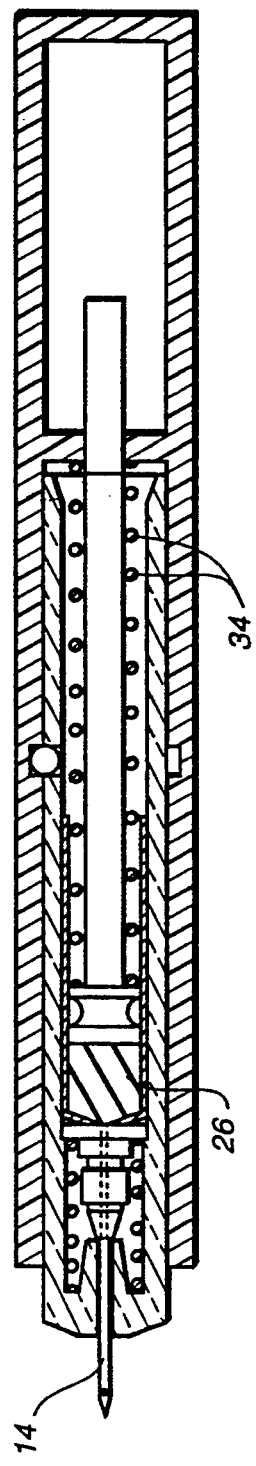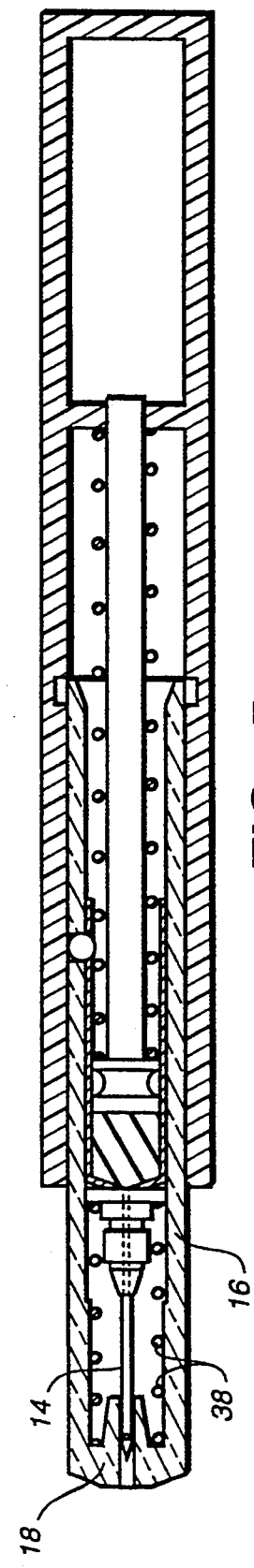

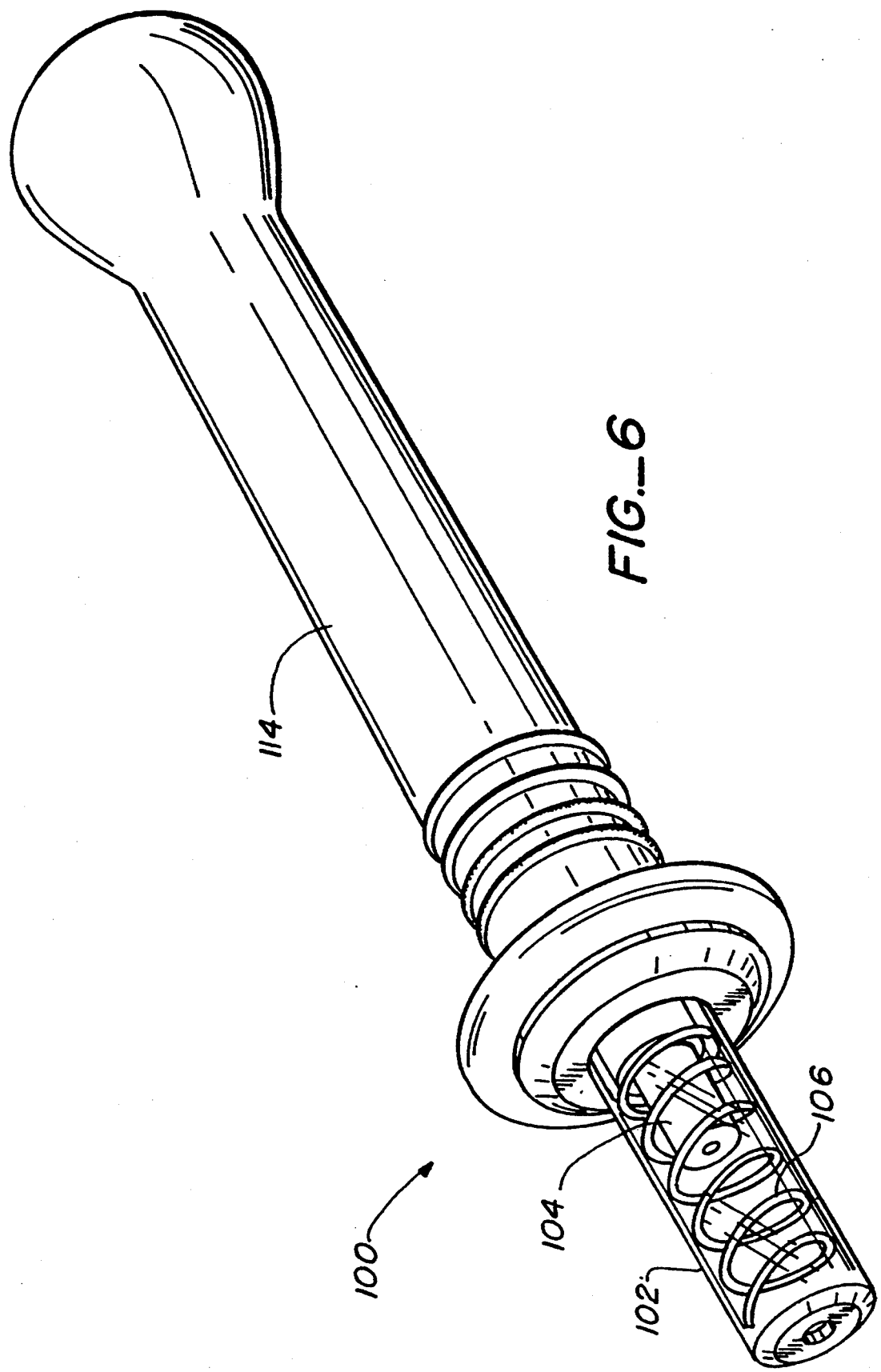
FIG._6

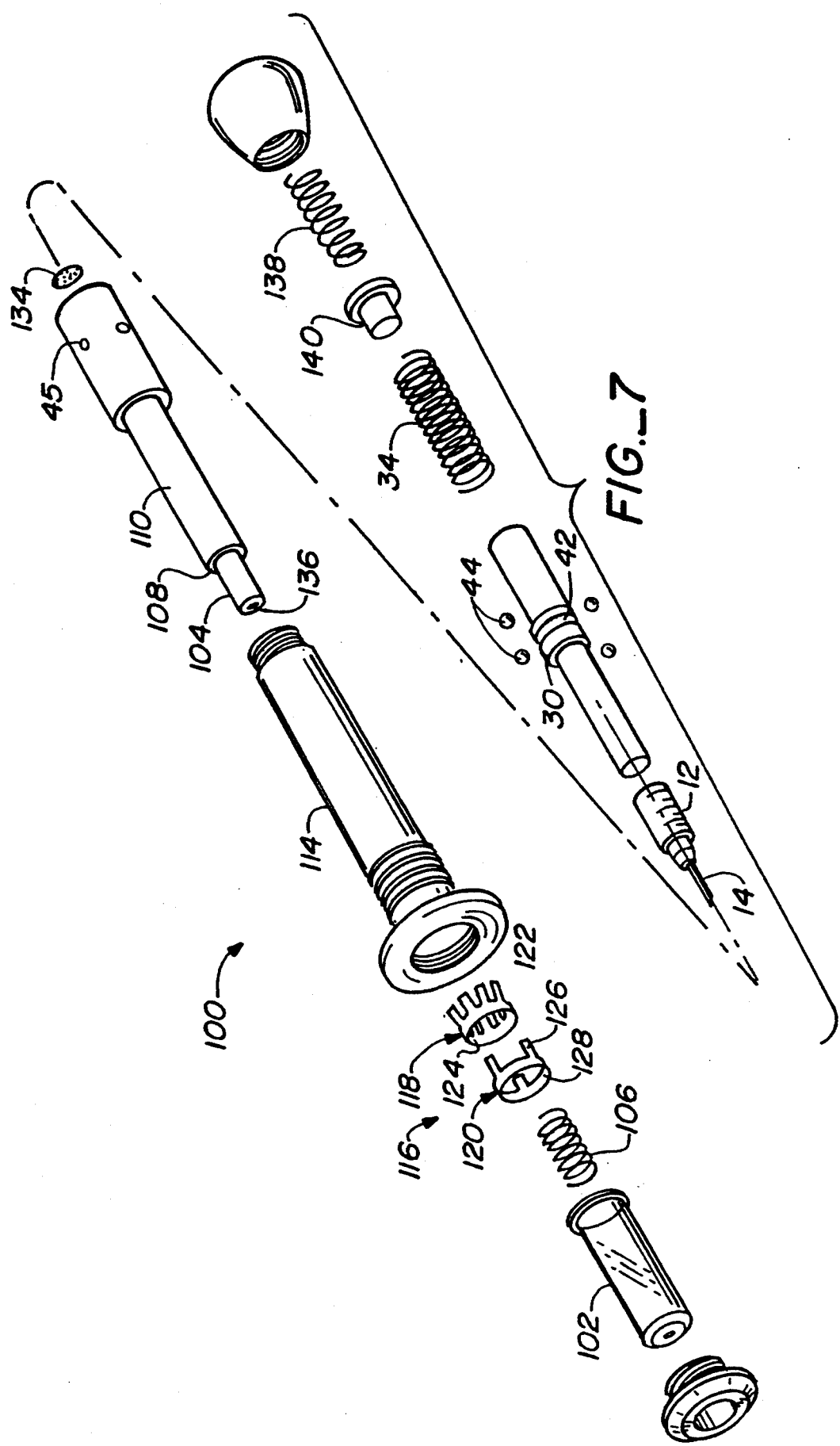
FIG._7

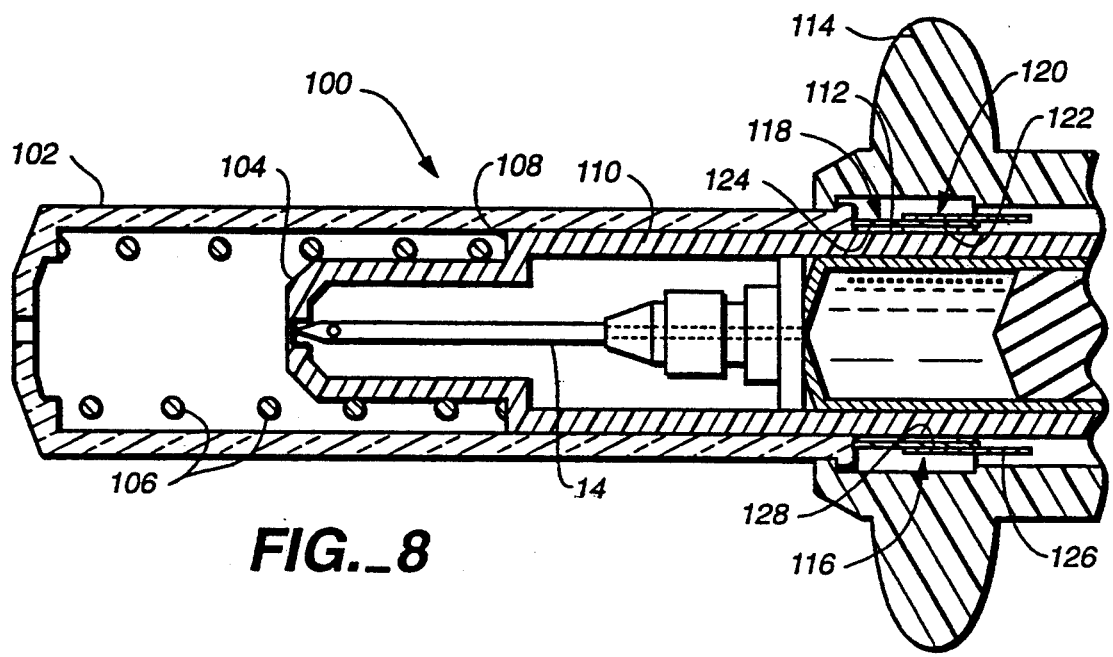
FIG._8
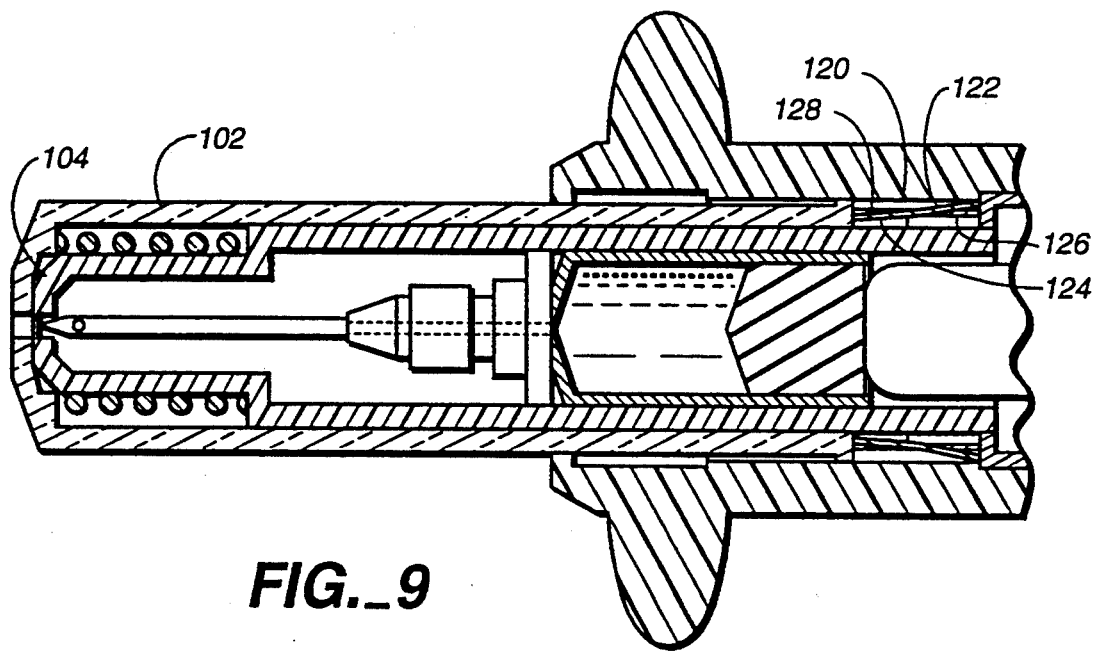
FIG._9

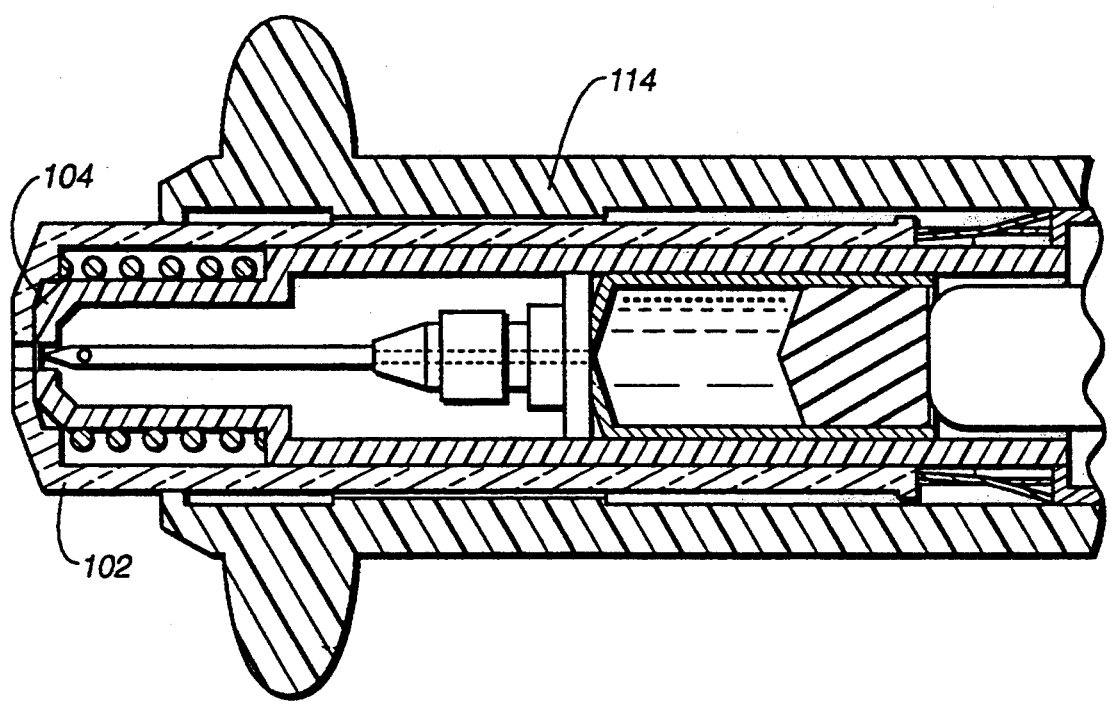
FIG._10

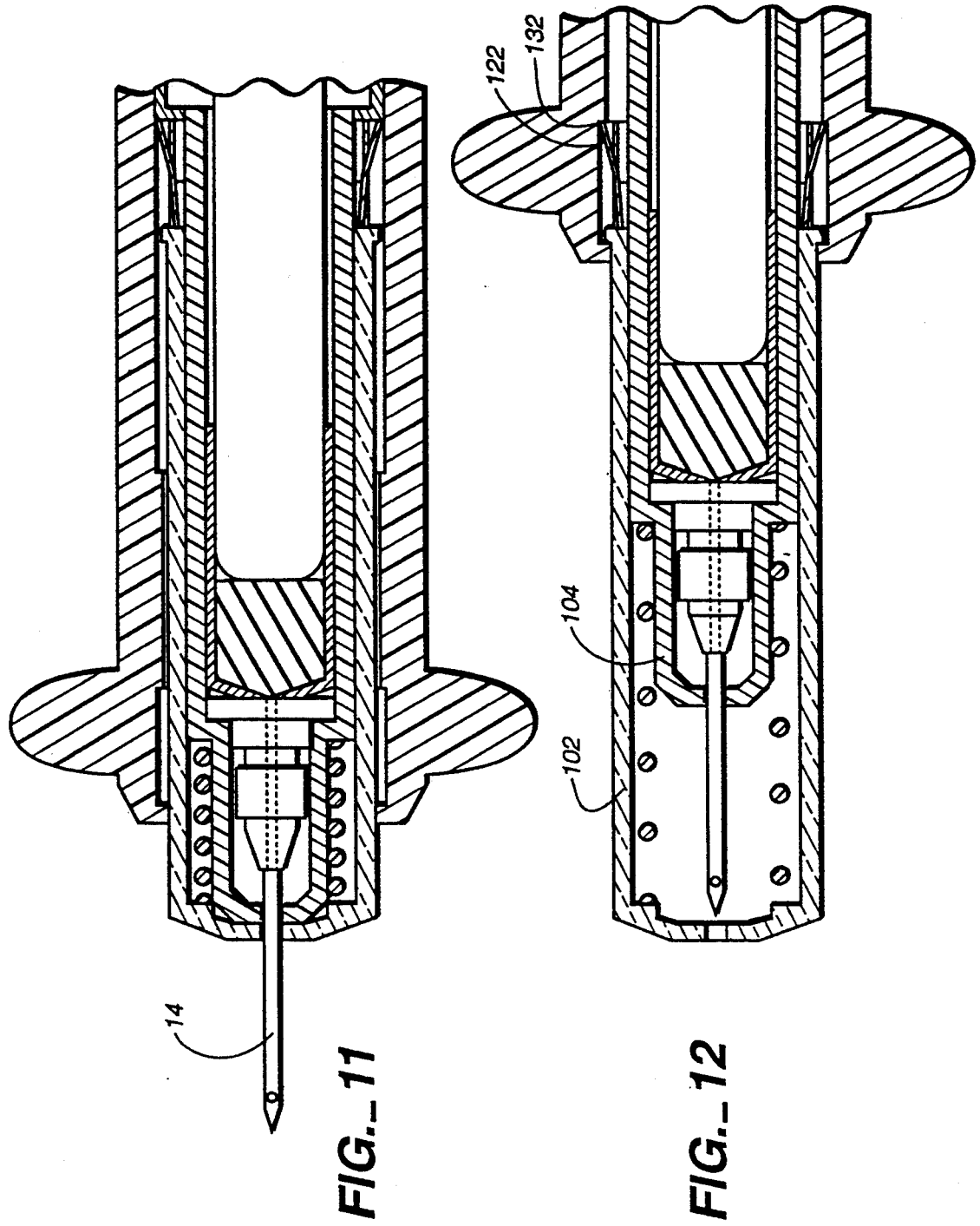

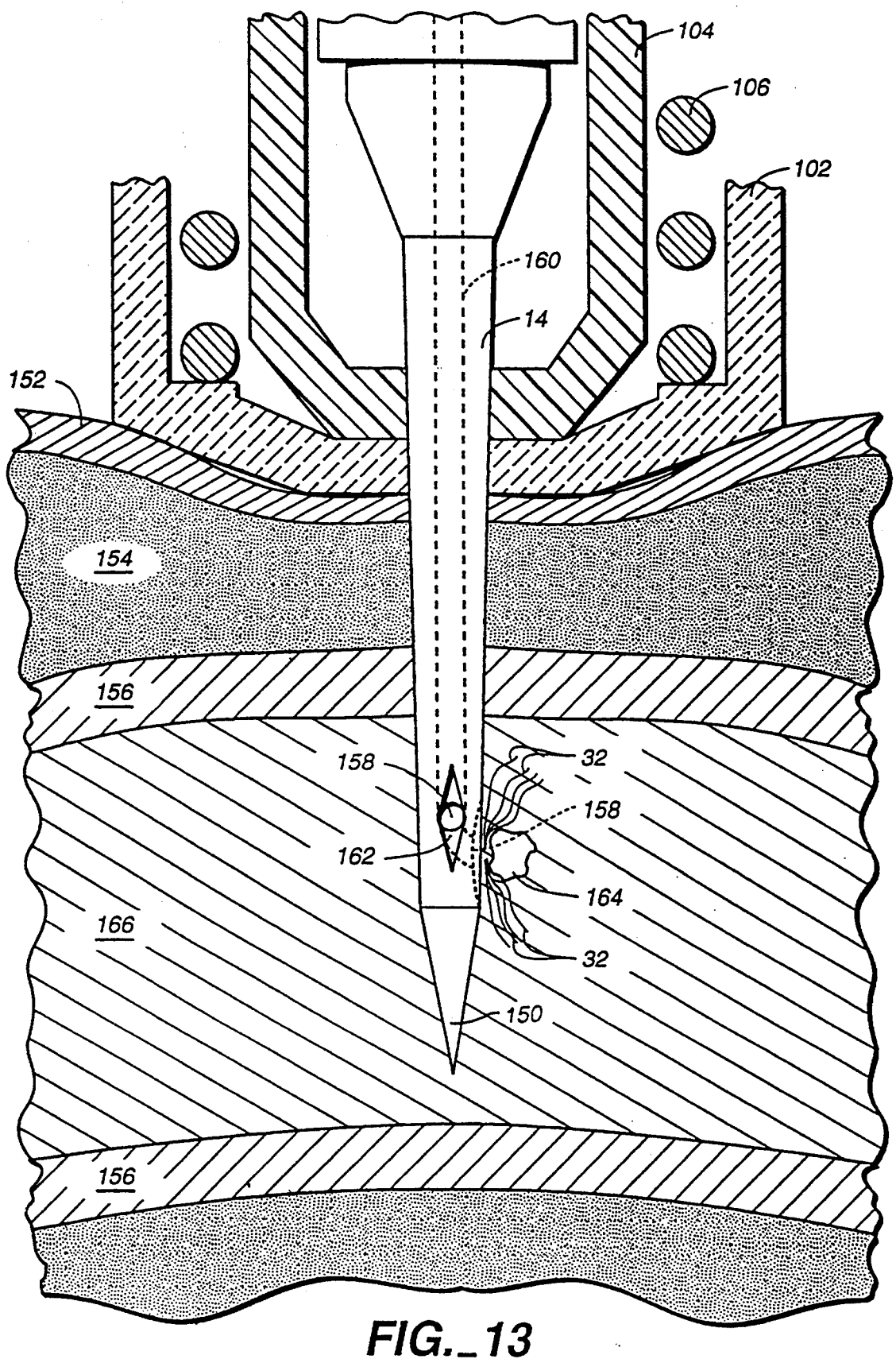
FIG._13

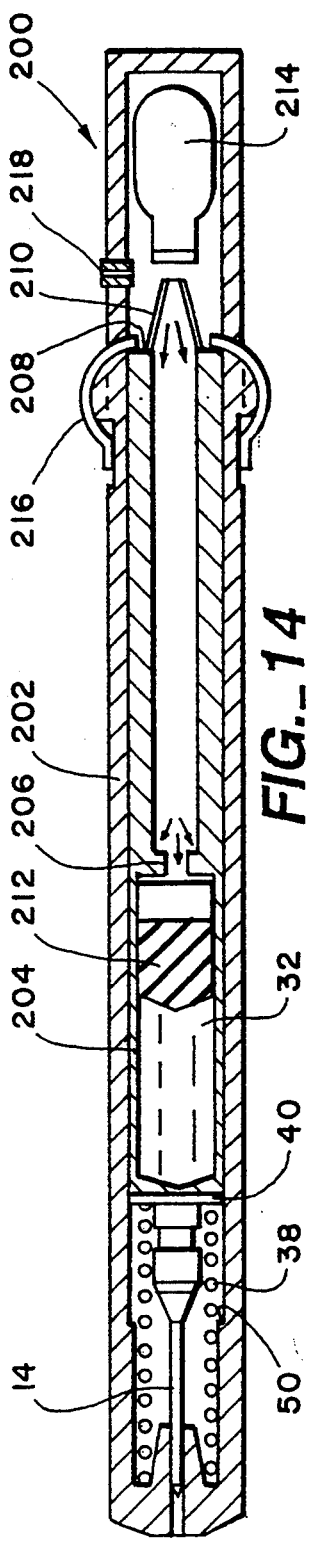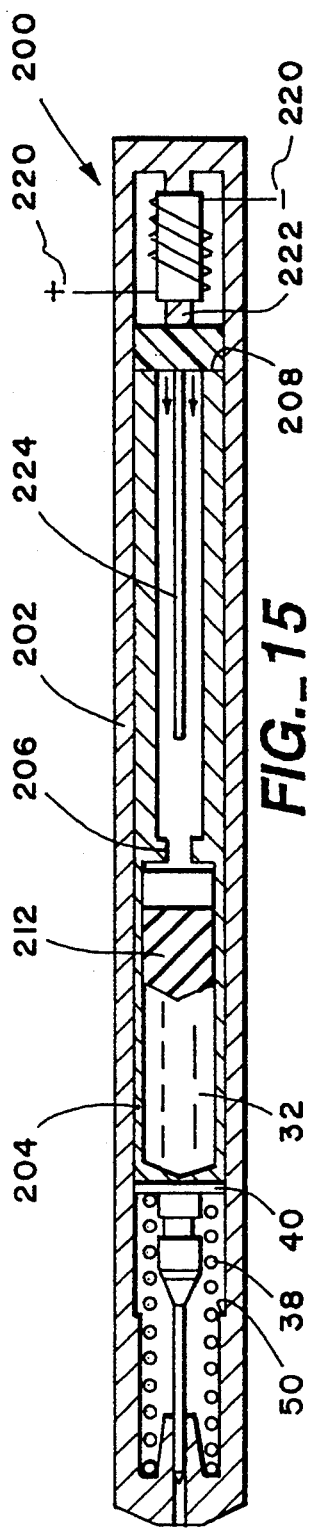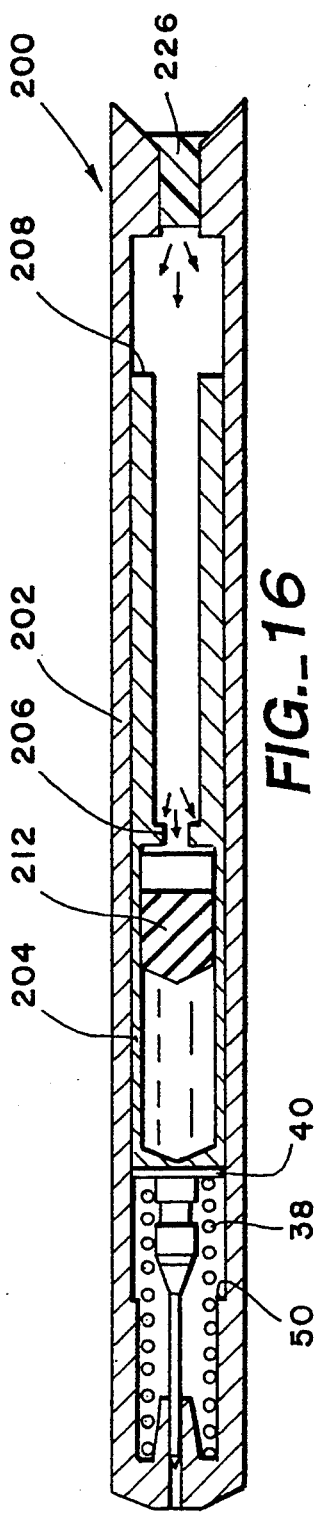

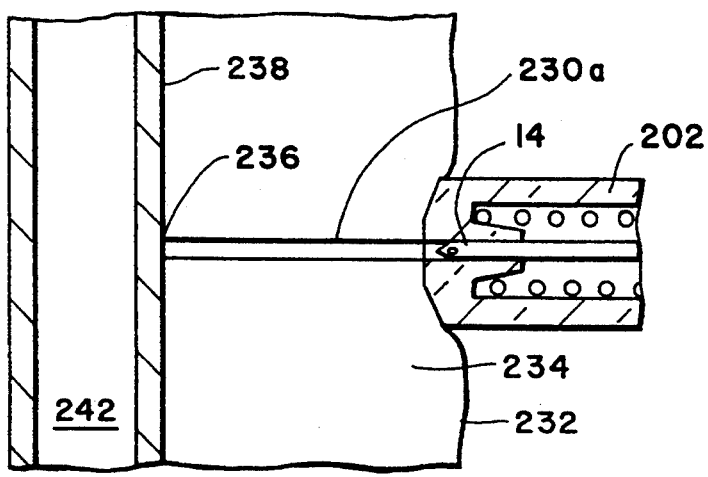
FIG._17
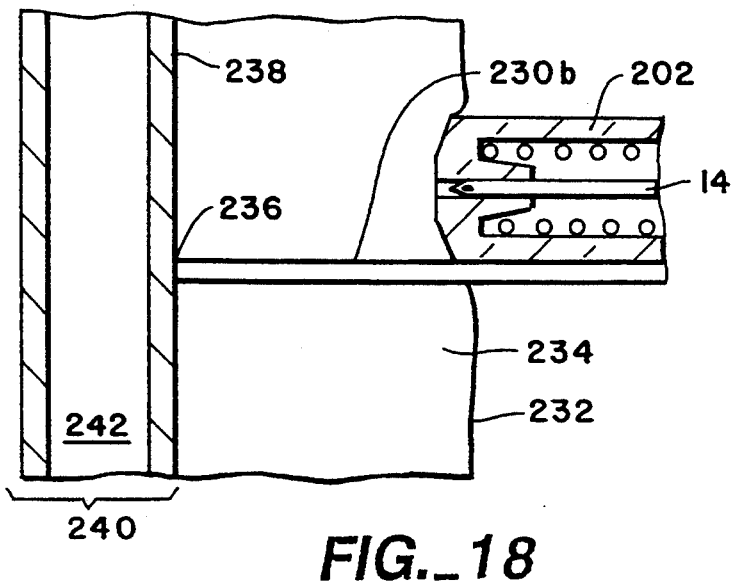
FIG._18
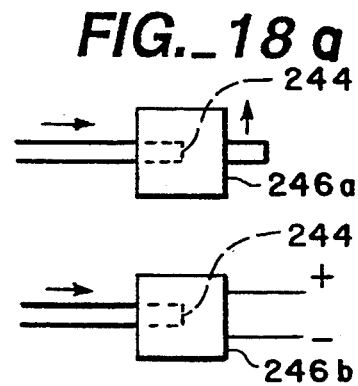
FIG._18a
FIG._18b
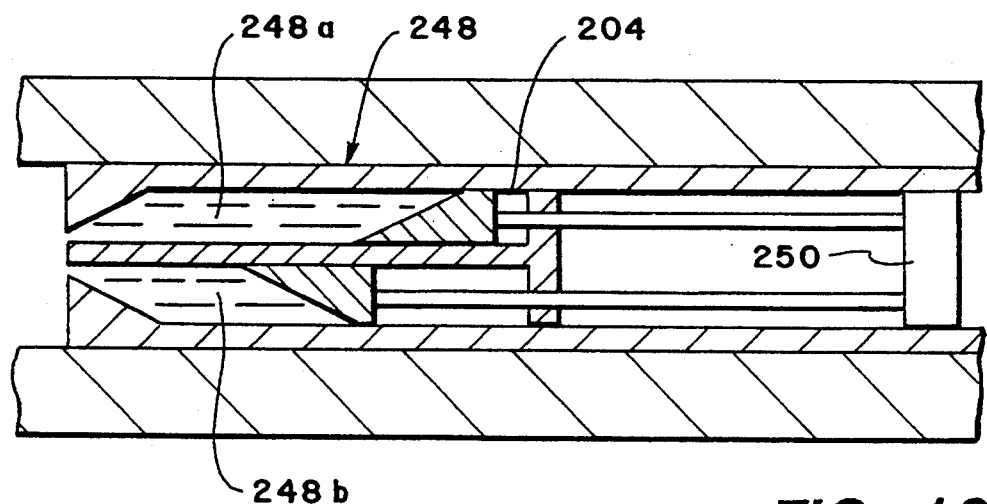
FIG._19

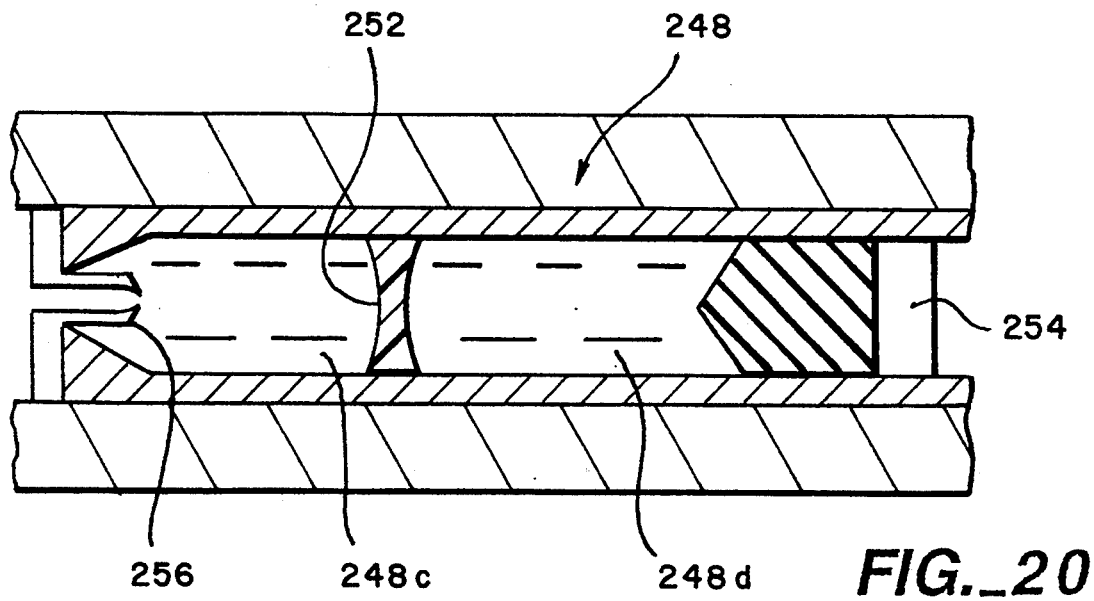
FIG._20
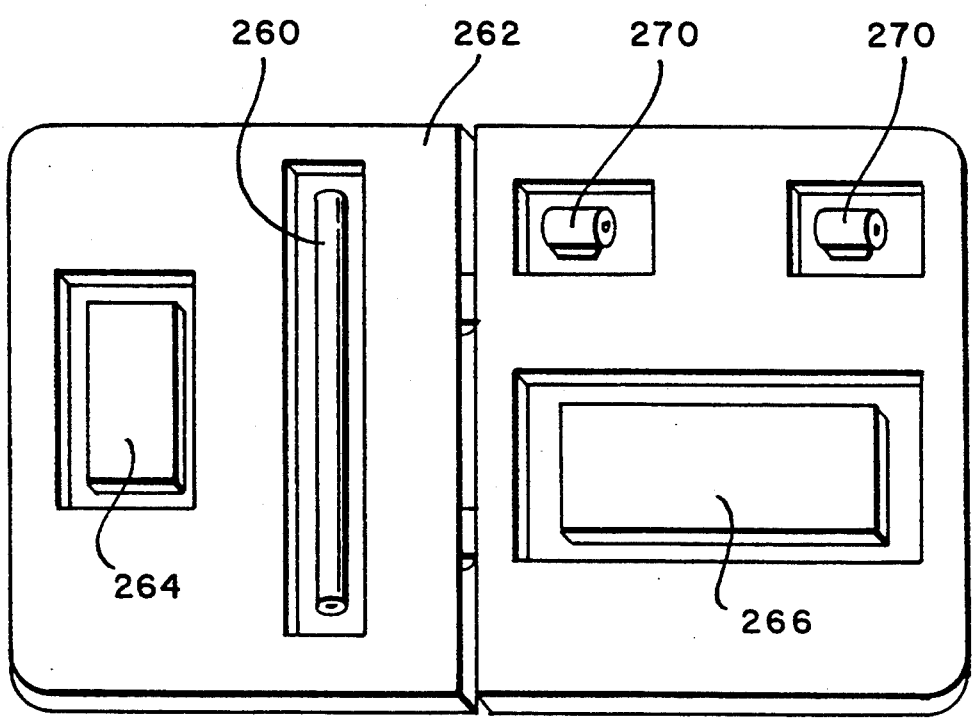
FIG._24

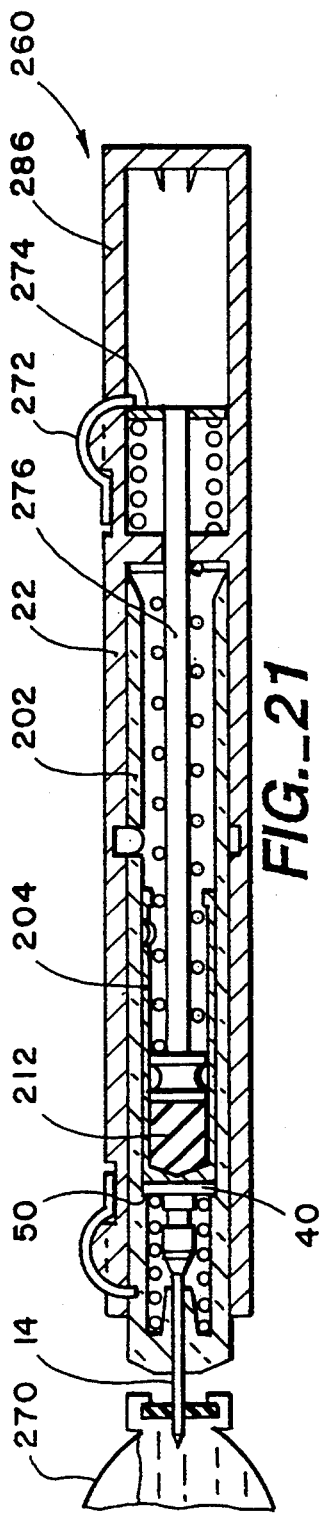
FIG._21
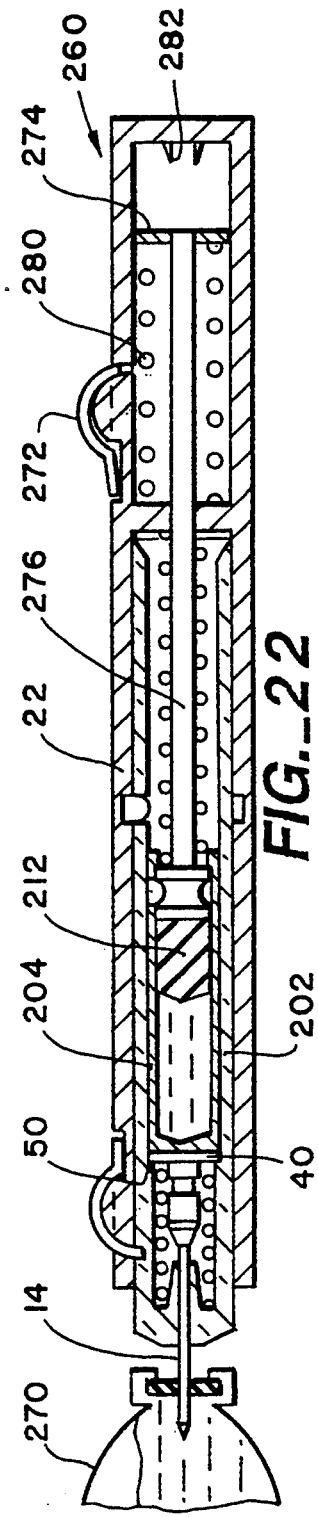
FIG._22
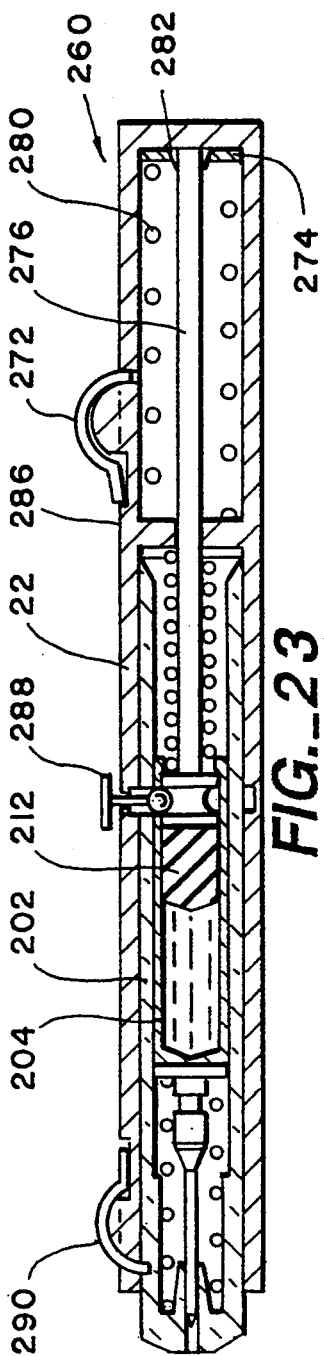
FIG._23

SYSTEM AND METHOD FOR RAPID VASCULAR DRUG DELIVERY

BACKGROUND OF THE INVENTION

This application is a continuation-in-part of Ser. No. 958,279, filed Oct. 8, 1992, now U.S. Pat. No. 5,211,744, which is a divisional of Ser. No. 692,674, filed Apr. 29, 1991 and issued Jan. 5, 1993 as U.S. Pat. No. 5,176,643.

1. Field of the Invention

This invention relates to a system and method for delivering fluids to the vascular system by infusion into bone marrow.

2. Background of the Relevant Art

It is well know that certain drugs, when given in a timely manner, can prevent death or minimize recovery time of a patient. Most resuscitating drugs are infused intravenously. However, intravenous infusion is not always easily accomplished. Oftentimes, persons requiring professional skills and training are needed in order to perform the intravenous procedures. In emergency situations, intravenous access cannot be achieved in a quick and safe fashion thereby adding to the failure rate of what should be resuscitating, life-saving drugs. Additionally, a vein may collapse as a result of low blood pressure thereby making it difficult to locate and access.

In an effort to overcome the problems of intravenous infusion, various catheters have been designed which can be more permanently placed into the vein or tissue. The catheters can be readily located and accessed through a membrane which covers a catheter port, wherein the catheter port is usually placed directly under the patient's skin. Unfortunately, subcutaneous catheters often result in infection and clotting at the vein-puncture site. Further, these devices often require minor surgery for insertion and removal. As a result, more permanent bone infusion devices have been developed. Such devices, often called "intramedullary catheters" or "intraosseous catheters", are used to allow direct infusion of fluid into the vascular system via bone marrow. Intramedullary catheters are well suited for rapid delivery of fluids into bone marrow. Examples of intramedullary devices, in general, are disclosed in Turkel U.S. Pat. No. 2,426,535; Young U.S. Pat. No. 2,773,500; Pshenichny et. al. U.S. Pat. No. 3,750,667; and Kramer et al. U.S. Pat. No. 4,969,870. A more permanently placed intramadullary device which can receive multiple infusions over a long period of time is disclosed in U.S. Pat. No. 4,772,261 to Von Hoff, et al. Additionally, numerous articles are written regarding intraosseous or intramedullary infusion procedures, a listing of several such articles are as follows: Tocantins, L. M. and O'Neill, J. F., "Infusion of Blood and Other Fluids into the General Circulation Via the Bone Marrow," *Surg. Gynecol. Obstet.*, 73, 281-2987 (1941); Turkel, H. and Bethell, F. H., "A New and Simple Instrument for Administration of Fluids Through Bone Marrow," *War Medicine*, 5, 222-225 (1944); Glaeser, P. W. and Losek, J. D., "Intraosseous Needles: New and Improved," *Pediat. Emerg. Care*, 4, 135-136 (1989); Sacchetti, A. D., Linkenheimer, R., Lieberman, M., Haviland, P , Kryszozak, L. B., "Intraosseous Drug Administration: Successful Resuscitation from Asystole," *Pediat. Emerg. Care*, 5, 97-98 (1989); Halvorsen, L., Bay, B. K., Perron, P. R., Gunther, R. A., Holcroft, J. W., Blaisdell, F. W., Kramer, G. C., "Evaluation of an Intraosseous Infusion Device for the Resuscitation of Hypovolemic Shock," *J. Traum.*, 30, 652-659 (1990).

Although bone marrow infusion systems provide many advantages over intravenous devices, intraosseous/intramedullary infusion often requires great skill and training for proper insertion and use. Moreover, intraosseous, as well as intravenous infusion requires many seconds to many minutes to insert and use. In an effort to overcome the lengthy insertion and injection process, many auto-injection syringes which place drugs into muscular or soft-tissue areas are disclosed in U.S. Pat. Nos. 3,396,726 to Sarnoff; 3,712,301 to Sarnoff; 3,882,863 to Sarnoff, et al.; and 4,031,893 to Kaplan, et al.

While auto-injection syringes, many of which are described above, are useful for rapid delivery of a drug into soft-tissue (muscle or skin), the auto-injectors are purposely unable to rapidly inject fluid into bone marrow. Injection into bone marrow would provide more rapid dissemination of any drug throughout the vascular system and therefore would enjoy the advantage of a higher resuscitation rate. Therefore, it would be advantageous to provide an auto-injection syringe capable of rapid placement of a fluid into the vascular system via direct bone marrow infusion. It would be further advantageous to provide a bone infusion syringe which can optimally place the distal end of the syringe needle into specific areas of bone marrow taking into account varying thickness of overlying tissue. It would be still further advantageous to provide a bone infusion syringe which can withdraw fluid from a fluid container, such as a vial, and then releasibly insert the needle into bone marrow and thereafter inject the drawn fluid into the marrow. The bone infusion syringe must be designed so as to prevent accidental exposure of the needle tip in order to minimize the likelihood of puncturing the administrator.

SUMMARY OF THE INVENTION

The problems outlined above are in large part solved by the bone infusion system and method of the present invention. That is, the infusion device hereof allows a user to quickly insert resuscitating fluids into the bone marrow in order to allow faster dissemination of the fluids throughout the circulatory/vascular system. The infusion device is therefore well suited for delivery of drugs necessary to resuscitate critically ill patients when vascular access is not already established. The infusion device can be used, if necessary, by lay personnel or personnel minimally trained in advanced first aid and cardiopulmonary resuscitation. Difficulties associated with intravenous access (i.e., infection, thrombosis, accidental injection to surrounding tissue, etc.) are substantially minimized by the bone infusion device hereof which can be directed to an easily and readily detected large target area, such as a sternum or tibia.

It is an object of the present invention to provide an intraosseous or intramedullary infusion device which can automatically and quickly puncture a bone containing marrow, place the needle into the marrow, and infuse fluid into the circulatory system via the marrow. After use, the device automatically retracts the needle so as to prevent accidental needle punctures by the user or patient. The device is well suited to compress the skin over the bone area in order to reduce the anatomical variability of skin overlying the bone. Alternatively, in situations where tissue interposed between the skin and bone greatly varies, a sensor or trigger needle can be used to locate the outer surface of the underlying bone and thereafter trigger the bone-puncture needle to a specified depth through the skin and tissue, and into the bone. In such a manner, the distal end of the puncture needle is placed at an optimal location within soft marrow in order to enhance fluid disbursement within the marrow and throughout the circulatory system.

It is yet a further object of the invention to provide such an infusion device which imparts velocity to the needle and syringe components in order to place the needle through the bone and into the marrow. The needle therefore is releasibly extended from the syringe device with sufficient momentum at the point of impact with the bone to allow for the needle to penetrate the bone. By releasibly extending the needle, the needle can develop sufficient velocity and momentum in order to allow smaller gauge needles to be used. Smaller gauge needles can pierce the bone with minimal destructive force. Momentum not only allows for a smaller gauge needle, but also ensures rapid placement at a specified depth (i.e., stroke length) into the underlying soft bone marrow.

It is yet a further object of the invention to provide such a bone infusion device which can accommodate numerous types of motive forces necessary for driving the needle, and can accommodate numerous configurations of fluid compartments within the needle syringe. As defined herein, "motive force" is any force necessary to drive the bone-infusion needle at a rapid rate from a locked position to an extended position and subsequently drive fluids from the fluid compartment or compartments through the extended needle. Motive forces include, but are not limited to, spring force, gas-expansive force, electro-mechanical force, etc. Not only can numerous motive forces be used to extend the needle with momentum through the bone impact area, but other motive forces can be used to withdraw fluid from a fluid container or body cavity through an extended needle and into the syringe fluid compartment. Thus, the infusion device can be used to withdraw or harvest fluids from one or more non-physiological or physiological fluid containers, whereby fluid drawn into the infusion device can be subsequently injected into another cavity or container area.

Broadly speaking, the present invention contemplates a device for rapid drug delivery in liquid form. The device includes a main housing with a front end and an aperture on the front end. A syringe body is further included having a front end and a rear end. The syringe body is slideably positioned in the main housing. A needle is attached to the front end of the syringe body, wherein the needle communicates with an interior of the syringe body and is positioned to extend through the aperture. A drive plunger extends from the rear end of the syringe body, and a means on the main housing is provided for locking and unlocking the drive plunger into and from, respectively, a position near the rear end of the syringe body. Another means, connected to the drive plunger, is provided for applying propelling force to the drive plunger necessary to move the syringe body along the main housing in a forward direction to extend the needle from the aperture and to subsequently expel the drug from the syringe body into the bone marrow. A further means is connected on the syringe body for moving the syringe body in a rearward direction opposite to the forward direction for withdrawing the needle into the aperture after injection is complete.

The invention further contemplates a device for delivery of a drug in liquid form to bone marrow, wherein the device has a main housing with a front end. A syringe body is slideably positioned in the main housing, wherein the syringe body includes a front end and a rear end. A needle is connected to the front end of the syringe body, wherein the needle includes a central bore communicating with at least one opening proximate to a tip of the needle. The needle further communicates with an interior of the syringe body and is positioned to extend through the aperture of the main housing an approximate distance necessary for passing through a patient's skin, penetrating a bone and entering marrow inside the bone. A means is used to impart a force to the syringe body and the attached needle in order to extend the needle through the aperture of the main housing a measured distance and at a sufficient velocity to pass through the patient's skin, penetrate the bone and enter the marrow. A means is further included to discharge drug in liquid form from the syringe, through the needle and into the marrow.

The present invention still further contemplates a needle for use in a device for delivery of a drug in liquid form. The needle has a body with a taper along its length and a conical orifice-free tip. A central bore communicates with a plurality of orifices proximate to the tip, and the plurality of orifices are positioned circumferentially on the needle at different distances from the tip.

The present invention yet further contemplates a method for delivering a drug in liquid form to bone marrow. The method includes the steps of positioning a syringe including a needle above a patient's skin at a location over a bone containing marrow. Sufficient velocity is imparted to the syringe so that the needle will have momentum necessary to pass through the patient's skin, penetrate the bone and enter the marrow. Velocity therefore pre-exists prior to the needle's point of impact with the patient's skin, bone and marrow. A drug, preferably in liquid form, is discharged from the syringe through the needle and into the marrow.

The present invention yet still further contemplates a device for injecting a fluid. The device comprises a main housing which includes an aperture at a front end of the main housing and a needle configured within the main housing. The needle is capable of being releasibly extended through the aperture with sufficient momentum at a point of impact to penetrate bone. The device further comprising means placed on the main housing for locking the needle within the main housing and for releasing the needle through the aperture. Means for releasing the needle comprises a trigger release mechanism, wherein the trigger release mechanism is coupled to a rear end of a trigger needle. The trigger needle further includes a forward end which is adapted to penetrate soft-tissue and bear against an outer surface of the bone while not penetrating the bone. Rearward movement of the trigger needle causes activation of the trigger release mechanism thereby releasibly extending the needle (bone-piercing needle) a specified distance within the bone.

The present invention yet still further contemplates a syringe body slideably positioned within the main housing. The syringe body partially surrounds at least two chambers in fluidic communication with the needle. The chambers are arranged parallel to each other such that, after the needle is releasibly extended, fluid is simultaneously expelled from the chambers. Alternatively, the chambers are arranged in series, for example, along a logitudinal axis such that, after the needle is releasibly extended, fluid in one chamber is expelled after fluid in another chamber is expelled.

The present invention yet sill further contemplates a device for drawing and injecting liquid into and from, respectively, a syringe body. The device comprises a syringe body having a syringe body front end and syringe body rear end slideably positioned in a main housing. The syringe body front end includes a needle attached thereto, and the needle is positioned to extend from and withdraw into the main housing. A drive plunger having a plunger front end and a plunger rear end is further provided, wherein the plunger front end is slideably positioned in the syringe body and the plunger rear end is releasibly coupled to a first motive force. The first motive force is capable of engaging the drive plunger rearward from the syringe body front end and subsequently the needle rearward into the main housing. A second motive force is provided and coupled to the plunger front end for engaging the needle forward from the main housing after the plunger rear end is released from the first motive force, and for subsequently moving the plunger front end forward toward the syringe body front.

The present invention yet further contemplates a method for withdrawing a fluid from a fluid container. The method comprises the steps of providing a syringe body having a syringe body front end and a syringe body rear end slideably positioned in a main housing. A needle is positioned upon the syringe body front end and into a fluid container. A plunger is then releasibly drawn within the syringe body from the syringe body front end to the syringe body rear end causing fluid to be drawn from the fluid container through the needle and into the syringe body. Continuing the step of drawing the plunger within the syringe body further causes the syringe body and connected needle to retract within the main housing. A further step of injecting fluid into the bone from the syringe body can be included, the injecting step comprises the steps of releasibly extending the needle from the main housing with sufficient momentum at the point of impact to penetrate bone. Continuing the step of releasibly extending the needle from the main housing causing the plunger to releasibly move within the syringe body from the syringe body rear end to the syringe body front end causing fluid to inject from the syringe body through the needle and into the bone.

BRIEF DESCRIPTION OF THE DRAWINGS

Other objects and advantages of the invention will become apparent upon reading the following detailed description and upon reference to the accompanying drawings in which:

FIG. 1 is a cross-sectional view of an exemplary embodiment of a device for rapid vascular drug delivery according to the present invention;

FIGS. 2-5 are similar cross-sectional views of the device of FIG. 1 at different stages in its use;

FIG. 6 is an external perspective view of another exemplary embodiment of the device for rapid vascular drug delivery according to the present invention;

FIG. 7 is an exploded perspective view of the device of FIG. 6;

FIGS. 8-12 are cross-sectional views of a portion of the device of FIGS. 6-7;

FIG. 13 is an enlarged side-view of a portion of the devices of FIGS. 1-12 in use;

FIGS. 14-16 are cross-sectional views of yet further exemplary embodiments of the device for rapid vascular drug delivery according to the present invention;

FIGS. 17-18 are cross-sectional views of embodiments for a triggering needle necessary for detecting the depth of the bone outer surface according to the present invention;

FIGS. 18a-18b are plan views of various trigger release mechanisms adapted for detecting movement of the triggering needles of FIGS. 17 and 18 and for releasing motive force upon the bone-piercing needles according to the present invention;

FIGS. 19-20 are cross-sectional views of various embodiments of fluid chambers within a syringe body necessary for expelling multiple fluids in parallel or in series according to the present invention;

FIGS. 21-23 are cross-sectional views of yet further exemplary embodiments of the device for rapid vascular drug delivery which is capable of withdrawing fluid from a fluid container into the syringe body according to the present invention; and FIG. 24 is a perspective view of a diagnostic or therapeutic device packaged with a device for rapid vascular drug delivery and/or withdrawal according to the present invention.

DETAILED DESCRIPTION OF THE INVENTION

Turning now to the drawings and more particularly to FIG. 1, there is shown a device 10 for rapid vascular drug delivery through, for example, the sternum or the tibia. Device 10 incorporates a cylindrical syringe body 12, fitted with a double side-holed pencil point needle 14. The syringe body is held in a cylindrical main housing 16 having a front barrel 18 with an orifice 20 through which the needle 14 may be extended. A cylindrical actuation handle 48 fits over end 24 of the main housing 16 for sliding movement along the main housing. A syringe plunger 26 contacts drive plunger 28 and extends into the syringe body 12 to confine liquid medication 32 in the syringe body 12. A motive force (i.e., main spring 34) extends between the drive plunger 28 and partition 36 on the actuation handle 48 to bias the actuation handle 48 in its extended position along the main housing 16 as shown in FIG. 1. A needle return spring 38 extends between the front barrel 18 and a collar 40 on the syringe body 12 to bias the needle to its retracted position as shown in FIG. 1. The main spring 34 exerts a stronger biasing force when compressed than the needle return spring 38. The drive plunger 28 has an annular peripheral socket 42 adapted to receive one or more lock balls 44, which engage one or more openings 45 on the main housing 16 to lock the drive plunger in position with respect to the syringe body 12. A mating annular lock ball trip pocket 46 is positioned on the inside surface of actuation handle 48 to allow the device 10 to be fired when the lock ball(s) in socket 42 reach the pocket 46. In FIG. 1, the device 10 is shown in its uncocked position.

In use, the device 10 is placed with the end of the front barrel 18 on, e.g., the midline of the sternum at the second or third intercostal space, and then the device 10 is pushed against the sternum. Device 10 can be placed in any large target area. An alternate target area includes the tibia medial area of any "long-bone" area of a physiological body. Compression of the spring 34 behind the syringe body 12 occurs as the front barrel 18 is pushed toward the actuation handle 48 and generates a force that will be used for needle 14 advancement and drug 32 injection. When an adequate force has been stored in the spring 34, the front barrel 18 has been pushed back to a point so that the lock ball(s) 44 are able to enter the trip pocket 46, as shown in FIG. 2. This entry releases the lock ball(s) 44, so that the main spring 34 is free to drive the syringe body 12 and the needle 14 forward with a force of about 25 to about 40 pounds until collar 40 rests against ridge 50, as shown in FIG. 3. The needle 14 can be extended from about 8 mm to about 16 mm in order to ensure that side holes in the forward end of needle are placed in the soft bone marrow. The main spring 34 then pushes the syringe plunger 26 forward to the position shown in FIG. 4 to deliver the drug 32 through the extended needle 14 to the marrow in the sternum. Needle placement takes about 1/10th of a second, while drug delivery usually occurs in less than a second. Operation in this manner causes the syringe body 12 to reach a sufficient velocity so that the penetration of the needle 14 into the marrow occurs in a single, rapid, uninterrupted motion due to momentum of the syringe body 12 and needle 14. Relying on momentum in this manner allows a smaller diameter needle to be used with less destruction to the bone than would be required if the penetration resulted from application of penetration force on the needle while it was at rest against the skin or bone. Upon completion of drug delivery, the operator releases pressure against the skin and bone, and the needle retraction spring 38 withdraws the needle 14 into the barrel 18 of the main housing 16 to the position shown in FIG. 5.

FIGS. 6–12 show another exemplary device 100 for the rapid delivery of a drug into bone marrow. The device 100 incorporates a locking, cylindrical protective cover 102 over front barrel 104 to insure that needle 14 is never exposed except when the device 100 is both pressed against the patient's body and actuated. A cover return spring 106 is positioned between the protective cover 102 and shoulder 108 on cylindrical main housing 110 of the device. The protective cover 102 has an end 112 that extends into actuation handle 114 of the device 100. End 112 is equipped with a tab locking mechanism 116 that, once actuated, prevents the protective cover 102 from being moved from its extended position as shown in FIG. 8 to its withdrawn position, against the barrel 104, as shown in FIG. 9. The locking mechanism 116 consists of two parts: a lock 118 circumferentially positioned around the end 112 between the protective cover 102 and the actuation handle 114, and a sleeve 120 concentrically positioned over the lock 118. The lock 118 has a plurality of spring tabs 122 extending rearward of the actuation handle 114 from a cylindrical base 124. The sleeve 120 has a plurality of projections 126, which are not springs, extending rearward beyond the tabs 122 from a similar cylindrical base 128. With the parts of the device 100 in the positions shown in FIG. 8, prior to use of the device 100, the cylindrical base 128 of the sleeve 120 rests over the spring fingers 122 of the lock 118, holding them down. As shown in FIG. 7, a sealing membrane 134 is provided inside the barrel 104, over orifice 136, to protect the needle 14 prior to use of the device.

In use of the device 100, with the spring fingers 122 in their down position, the protective cover 102 is free to retract against the barrel 104 to the position shown in FIG. 9, when the protective cover 102 is pressed downward against, e.g., the sternum or the tibia. As the protective cover 102 moves toward the barrel 104, the projections 126 of the sleeve 120 engage the actuating handle 114, so that the base 128 of the sleeve 120 is pushed down over the base 124 of the lock 118, allowing the spring fingers 122 of the lock 118 to spring outward as shown in FIG. 9. Continued downward pressure of the device 100 on the sternum or tibia moves the protective cover 102 and the barrel 104 into the actuating handle 114, as shown in FIG. 10, until the main body 108 and the actuating handle reach the firing position, as in the FIGS. 1–5 embodiment. At that time, firing occurs, the needle 14 is extended into bone and the fluid (e.g., liquid-form drug) is ejected into the marrow through the needle 14, as shown in FIG. 11 in the same manner as in the FIGS. 1–5 embodiment. When the device 100 is no longer pressed against the patient, the protective cover 102 is returned to its original position by the force of spring 106, as shown in FIG. 12. Because the spring tabs 122 have sprung outward, they engage shoulder 132 to lock the protective cover 102 over the needle 14. Thus, the needle is never exposed except when the device 100 is actually pressed against the patient, and the needle 14 cannot be re-exposed after actuation, even if the device is again pressed against the patient or an object. In addition to the main spring 34, a secondary spring 138, separated from the main spring by member 140, is provided to ensure that there is still a spring force urging the needle 14 forward when it is fully extended. Except as shown and described, the construction and operation of the FIGS. 6–10 embodiment of the invention is the same as that of the FIGS. 1–5. embodiment.

FIG. 13 shows details of the needle 14 used in the devices 10 and 100. The needle 14 has a slight taper along its length toward a conical, orifice-free tip 150. The taper promotes a good seal between the needle 14 and bone 156. The tip 150 of the needle 14 is free of an orifice because orifices located there would tend to clog during penetration of bone 156. Orifices 158 are located behind the conical tip 150 and communicate with a central bore 160 extending the length of the needle 14 to communicate with the reservoir of drug 32 (FIG. 1). The orifices 158 are staggered about the circumference of the needle 14 and connect to slits 162 extending vertically along the side of the needle. This configuration and placement of the orifices 158 and the slits 162 allow discharge of the drug 32 from an orifice 158, even if it is partially blocked by a tissue globule 164 in marrow 166.

Examples of drugs that can be life saving for specific medical emergencies if administered into the central circulation in a timely manner, and hence, candidates for packaging in devices 10 and 100, are shown in the following table:

| Drug | Medical Emergency |
|---|---|
| Epinephrine or related compounds | Cardiac arrest; Anaphylactic shock |
| Naloxone | Narcotic overdose |
| Atropine sulfate | Organophosphate poisoning |
| Benadryl | Anaphylactic shock |
| TPA (tissue plasminogen activator) | Myocardial infarction |
| Valium | Convulsion/seizures |
| Sodium pentobarbital | Convulsion/seizures |
| Lidocaine | Cardiac arrhythmias |

All of the above medical emergencies are and can be life threatening. The vascular delivery of the above drugs can be life saving. Even a few seconds delay in therapy can be a matter of life or death in the above emergencies. The described invention can administer these drugs into the circulation system, often in less than 1 or 2 seconds, can be safely and effectively performed by a lay person with minimal training and, overall, offers a safe, effective, automated and extremely rapid means to treat medical emergencies.

Because momentum is used to advance the needle through the cortical bone and into the marrow, even a small gauge needle, such as a 20 to 25 gauge, straight-walled, simple pencil point with multiple sideholes can be properly placed. Because the effective dose of most of the previously listed drugs could be carried in exceedingly small volumes, such as 0.1 to 0.2 ml or less, such a small gauged needle could be used for rapid drug delivery. Alternatively, a larger needle (12 to 18 gauge), either a simple pencil point or the design previously described could be used to rapidly administer 1.0 to 5.0 ml of fluid. The invention and these needles and drugs can be delivered effectively into circulation in as short a time as 1 to 2 seconds or less.

While the invention has been shown in FIGS. 1-13 in two preferred forms, various modifications of it could be made. For example, the device could be constructed so that it is cocked or loaded prior to placing it in contact with the patient, and merely fired after it is triggered and/or pressed against the patient with a suitable pressure. As such, a pre-loaded device is shown in the various embodiments of FIGS. 14-16. In particular, device 200, includes a main housing 202 necessary for containing a syringe body 204 and needle 14. The syringe body 204, shown in FIG. 14, includes inwardly protruding flanges 206 and rearward ends 208 necessary to accommodate piercing members 210. Syringe body 204, at a front end thereof, forms a fluid container bounded by syringe body 204 and syringe plunger 212. Piercing members 210 form an opening in compressed gas chamber 214 necessary to release the gas against flange 206 and thereby force syringe body 204 in a forward direction causing needle 14, connected to the front end of body 204, to releasibly extend from main housing 202. Accordingly, the exemplary embodiment of FIG. 14 describes a compressed gas motive force for driving needle 14 with sufficient momentum to penetrate a hard surface such as bone. After needle 14 penetrates bone, plunger 212 is forced forward by the compressed gas flow thereby driving fluid 32 from the fluid chamber, through needle 14 and into the bone marrow. Syringe body 204 is releasibly extended by activating a trigger mechanism 216 coupled to main housing 202, as shown. Release of trigger mechanism 216 allows spring 38 to drive piercing members 210 into chamber 214. Any excess compressed gas can be expelled by a release valve 218.

There are numerous types of motive forces capable of driving needle 14 in an extending position through bone, and for subsequently driving fluid 32 from syringe body 204. Another such exemplary motive force is illustrated in FIG. 15. Electro-mechanical force can be used to extend syringe body 204 by applying a voltage differential between electrodes 220. Electrical stimuli forces a magnetic yolk 222 in a forward direction causing movement of rearward end 208. After a specified distance, the forward end of member 224 contacts against plunger 212 causing expulsion of fluid 32.

Yet another exemplary motive force can be used to drive syringe body 204 and plunger 212. Such motive force is illustrated in FIG. 16 and includes an explosive chamber 226. When activated, chamber 226 releases pressure waves in the direction shown, against rearward ends 208, flanges 206 and plunger 212. Plunger 212 is not activated until collar 40 abuts against ridge 50, similar to the configurations of FIGS. 14 and 15. In each exemplary embodiment shown and described, various motive forces can be used to extend needle 14 and, subsequently, inject fluid 32 through needle 14 in addition to the main spring 34 motive force shown in the embodiments of FIGS. 1-7 above. It should now be readily apparent to those skilled in the art that any motive force is suitable provided the force can releasibly extend needle 14 with sufficient momentum to penetrate bone. The releasing mechanism can be internal lock-balls, an external trigger, an electrical impulse, and/or a hammer-fire mechanism.

Turning now to FIGS. 17 and 18, exemplary embodiments of a trigger needle 230 are illustrated. As shown in FIG. 17, trigger needle 230a can be placed along the same logitudinal axis as needle 14. Trigger needle 230a is designed to manually pierce skin 232 and soft-tissue 234. Once forward end 236 of trigger needle 230a abuts against the hard cortical outer surface 238 of bone 240, trigger needle 230a moves rearward causing release of a triggering mechanism, described below.

Alternatively, trigger needle 230 can be arranged a lateral spaced distance from needle 14 along the outer surface of main housing 202, as shown in FIG. 18. Accordingly, movement of trigger needle 230b releases a triggering mechanism arranged on the outer surface of main housing 202. As would be obvious to a person skilled in the art, numerous ranges of a protruding trigger needle can be achieved for activating a trigger release mechanism and releasing a motive force upon the bone-piercing needle 14. Trigger needle 230 is suitably used to measure a distance between skin 232 and the outer surface of cortical bone 238 in order to ensure precise stroke length of needle 14 into an optimal location within marrow 242. As such, large fluctuations in anatomical make-up can be compensated for by a triggering needle 230 of the present invention. Regardless of the thickness of tissue 234, (providing tissue 234 is less than the length of trigger needle 230), trigger needle 230 will ensure proper placement of the forward end of needle 14 into marrow 242.

Referring now to FIGS. 18a and 18b, rearward ends 244 of trigger needle 230 are mechanically coupled (shown in dashed line) to a mechanical (FIG. 18a) or electrical (FIG. 18b) caming device 246a and 246b, respectively. The caming device can mechanically or electrically stimulate a trigger or input terminal arranged within the device or upon the outer surface of the device, a configuration which would be well-known to the skilled artisan. Thus, the triggering mechanism shown in FIGS. 18a and 18b are purposely suited to initiate the releasable motive force upon the needle and plunger.

Referring now to FIGS. 19 and 20, various embodiments and arrangements of two or more fluid chambers 248 are shown. Fluid chambers 248, shown in FIG. 19, can be arranged in parallel as chambers 248a and 248b. Forward movement upon plunger 250 causes separate, pre-loaded fluids within chambers 248a and 248b to be ejected from syringe body 204 in an intermixed fashion. One chamber, chamber 248a can, for example, be made larger than chamber 248b in order to accommodate a larger medicant dose.

Referring to FIG. 20, fluid chambers 248 can be arranged in series. In particular, chamber 248c can be placed at the front end of chamber 248d. Slideable membrane 252 is sealingly engaged against the syringe body inner walls and can be used to separate fluid within chambers 248c and 248d. Forward movement upon plunger 254 causes fluid within chamber 248c to be expelled first. Piercing members 256 will, upon forward movement of plunger 254, come in contact with and pierce member 252 thereby allowing fluid within chamber 248d to be expelled. For example, fluid within chamber 248d can be a saline fluid necessary to flush medicant within chamber 248c completely from syringe body 204 and deep within the bone marrow. Saline solution therefore acts to enhance the disbursement of a drug within chamber 248c into and throughout the bone marrow and vascular system.

Referring now to FIG. 24, various embodiments of a rapid vascular drug delivery device 260 (i.e., device 10, device 100 and device 200 described above) can be packaged in a wrapper or container 262 along with various other therapeutic or diagnostic devices 264 and 266, respectively. Container 262 can, if necessary, provide a hermetic seal in order to maintain sterility of device 260. Diagnostic devices such as detectors for cardiac arrest, narcotic overdose, organophosphate poisoning, anaphylactic shock, myocardial infarction, and various convulsions and seizures, all of which can be used to detect life-threatening events, can be packaged with the device 260. Therapeutic devices 264 can also be included, an exemplary therapeutic device includes a drug screening kit or a blood sugar test kit for monitoring therapeutic events and providing the required drug at proper moments via device 260. Ampules or vials 270 can also be provided in package 262, wherein the ampules or vials contain therapeutic fluids or drugs which can be withdrawn from their respective containers and placed into fluid chambers within syringe body 204, as shown in FIGS. 21–23.

Turning now to FIGS. 21–23, device 260 (i.e., devices 10, 100 and/or 200) can be retrofitted to allow withdrawal of fluid from container 270 through needle 14 and into a fluid chamber surrounded by syringe body 204 and plunger 212. Plunger 212 and syringe body 204 are retained in a forward direction such that collar 40 abuts against flange 50, as shown in FIG. 21. Trigger mechanism 272 insures syringe body 202 and connected needle 14 remain in a forward position in order to allow needle 14 to extend beyond main housing 202 and into container 270.

Activation of trigger mechanism 272 allows release of the rear end 274 of plunger rod 276. Plunger rod 276 thereby draws plunger 212 (forward end of rod 276) in a rearward direction, as shown in FIG. 22. Plunger 212 extends in a rearward direction until it abuts against inward facing protrusions 278. Thereafter protrusions 278 cause first motive force 280 (retraction spring) to further draw syringe body 204 in a rearward direction thereby retracting needle 14 from container 270, as shown in FIG. 23. Once the rearward end of plunger 274 is fully retracted, piercing members 282 sever end 274 thereby allowing forward motion of plunger rod 276 apart from end 274 and retractive motive force 280. Accordingly, a second motive force 284 coupled between the front end of plunger rod 276 (plunger 212) and actuation handle 286 forces syringe body 204 and plunger 212 in a forward direction to allow needle 14 to penetrate bone and inject fluid therein. A second trigger mechanism 288 can be used to retain needle 14 and plunger 212 in their drawn position until a time comes in which injection is desired. A third trigger 290 can be used to retain the relative positions of main housing 202 and actuation handle 286. By activating trigger 290, main housing 202 can be moved relative to actuation handle 286 in accordance with the design shown in FIGS. 1–12.

It is appreciated from the drawings of FIGS. 21–23, that various motive forces exerting in a forward or rearward direction can allow withdrawal of fluids from a container and subsequent injection of those fluids back into another container or physiological cavity, such as bone marrow. In both instances, withdrawal and injection can be achieved by triggering mechanisms which releasibly retract and extend needle 14 into a desired position. As shown throughout the embodiments describing a pre-loaded fluid chamber, it is understood that pre-loading of the fluid can occur in various ways. One way is to draw the fluid into the chamber using the bone piercing needle (as shown in FIGS. 21–23). Another way is to inject fluid, via a syringe, through main housing 202 and plunger 212 and into the cavity/chamber of syringe body 204.

It will be appreciated to those skilled in the art having the benefit of this disclosure that this invention is believed to be capable of withdrawing fluids and injecting fluids. Furthermore, the device, system and method hereof can withdraw fluids and subsequently retract a needle within a main housing. Thereafter, at a specified user-defined time, the device can releasibly extend the needle into a hard substance such as bone and subsequently inject the fluid into bone marrow. Numerous types of motive force can be used to retract and extend the bone-piercing needle as well as to draw or inject fluids into and from the present device. Furthermore, it is also to be understood that the form of the invention shown and described is to be taken as exemplary preferred embodiments. Various modifications and changes may be made without departing from the spirit and scope of the invention as set forth in the claims. It is intended that the following claims be interpreted to embrace all such modifications and changes and, accordingly, the specifications and drawings are to be regarded in an illustrative rather than a restrictive sense.

What is claimed is:

1. A device for inserting a bone-piercing needle port into bone, comprising:
   a main housing which includes an aperture at a front end of said main housing;
   a trigger needle having a forward end and a rear end, wherein said rear end is coupled to a trigger release mechanism mounted upon said main housing and said forward end is adapted during use to penetrate soft tissue and activate said trigger release mechanism upon bearing against a bone underlying said soft tissue; and
   a bone-piercing needle configured within said main housing, wherein said bone-piercing needle is coupled to said trigger release mechanism to releasibly extend through said aperture and into said bone during activation of the trigger release mechanism.

2. The device as recited in claim 1, wherein said bone-piercing needle is adapted to releasibly extend with sufficient momentum at the point of impact to penetrate bone and reside partially within a bone marrow cavity of said bone.

3. The device as recited in claim 1, wherein said bone-piercing needle comprises a bore and at least one orifice extending into said bore from the side of the bone-piercing needle.

4. The device as recited in claim 3, wherein said orifice is configured at one end of said bone-piercing needle in fluid communication with a bone marrow cavity of said bone.

* * * * *